United States Patent
Burd

(10) Patent No.: US 10,656,166 B2
(45) Date of Patent: May 19, 2020

(54) INHIBITING CHRONIC BLOOD AND NEPHROLOGICAL DISORDERS USING LYSINE-BASED SUPPLEMENTS

(71) Applicant: Lysulin, Inc., San Diego, CA (US)

(72) Inventor: John Burd, San Diego, CA (US)

(73) Assignee: Lysulin, Inc., San Diego, CA (US)

( * ) Notice: Subject to any disclaimer, the term of this patent is extended or adjusted under 35 U.S.C. 154(b) by 0 days.

(21) Appl. No.: 15/870,822

(22) Filed: Jan. 12, 2018

(65) Prior Publication Data

US 2019/0137519 A1 May 9, 2019

Related U.S. Application Data

(63) Continuation of application No. 15/870,813, filed on Jan. 12, 2018, which is a continuation-in-part of application No. 15/817,574, filed on Nov. 20, 2017.

(60) Provisional application No. 62/581,573, filed on Nov. 3, 2017.

(51) Int. Cl.
| | |
|---|---|
| *G01N 33/70* | (2006.01) |
| *A61K 47/64* | (2017.01) |
| *A23L 33/15* | (2016.01) |
| *G01N 33/66* | (2006.01) |
| *A23L 33/16* | (2016.01) |
| *A23L 33/175* | (2016.01) |
| *G01N 33/68* | (2006.01) |

(52) U.S. Cl.
CPC .............. *G01N 33/70* (2013.01); *A23L 33/15* (2016.08); *A23L 33/16* (2016.08); *A23L 33/175* (2016.08); *A61K 47/645* (2017.08); *G01N 33/66* (2013.01); *G01N 33/6896* (2013.01); *G01N 2800/347* (2013.01); *G01N 2800/52* (2013.01)

(58) Field of Classification Search
CPC ...... G01N 33/70; G01N 33/66; G01N 33/645; A61K 47/645; A23L 33/15; A23L 33/16; A23L 33/175
See application file for complete search history.

(56) References Cited

U.S. PATENT DOCUMENTS

| | | |
|---|---|---|
| 8,060,249 B2 | 11/2011 | Bear et al. |
| 2003/0082074 A1 | 5/2003 | Jurik et al. |
| 2004/0060859 A1 | 4/2004 | Seshimoto |
| 2007/0238770 A1 | 10/2007 | Gougoutas |
| 2008/0004507 A1 | 1/2008 | Williams, Jr. |
| 2008/0014644 A1 | 1/2008 | Barasch |
| 2008/0027024 A1 | 1/2008 | Gahler et al. |
| 2013/0035563 A1 | 2/2013 | Angelides |
| 2014/0044828 A1 | 2/2014 | Mine et al. |
| 2014/0227371 A1 | 8/2014 | Heath |
| 2014/0256806 A1 | 9/2014 | Tanaka |
| 2014/0363896 A1 | 12/2014 | Zuzuki |
| 2015/0038453 A1 | 2/2015 | Hageman et al. |
| 2015/0160218 A1* | 6/2015 | Demirci ........... G01N 33/54346 435/5 |
| 2015/0182483 A1* | 7/2015 | Goldberg ............. A61K 31/198 514/564 |
| 2016/0263317 A1 | 9/2016 | Arefieg |
| 2017/0061823 A1* | 3/2017 | Cohen .................... G16H 40/63 |
| 2017/0255758 A1 | 9/2017 | Washko |

FOREIGN PATENT DOCUMENTS

| | | | |
|---|---|---|---|
| CN | 101642468 | * | 2/2010 |
| CN | 102772215 | | 11/2012 |
| CN | 104138469 | | 1/2014 |
| WO | 2004035074 A1 | | 4/2004 |
| WO | 2005123108 A1 | | 12/2005 |
| WO | WO 2008/120797 | * | 10/2008 |
| WO | 2010017190 A1 | | 2/2010 |
| WO | 2011086507 A1 | | 7/2011 |

OTHER PUBLICATIONS

Examine.com, "Zinc", published online: Nov. 1, 2016; obtained via Internet Archive Wayback Machine on Apr. 26, 2018.*
Chen, CN 101642468; published: Feb. 10, 2010, English machine translation obtained on Apr. 26, 2018.*
Hirabayashi et al., WO 2008/120797, published: Oct. 9, 2008, English machine translation obtained on Apr. 26, 2018.*
Khayat, Y., "Anti-Glycation Supplements Part III (Glycation: Part II of II)," Perspectives on Health, Jan. 26, 2015 (Jan. 26, 2015), pp. 1-52. Retrieved from the internet: <https://yochanakhayat.wordpress.com/2015/01/26/anti-glycation-supplements-part-iii-glycation-part-ii-of-ii/> on Mar. 6, 2018 (Mar. 6, 2018). entire document.
International Search Report and Written Opinion corresponding to International PCT Application No. PCT/US2018/015587 dated Apr. 13, 2018.
NHS, Point-of-care Creatinine Testing for the Detection and Monitoring of Chronic Kidney Disease, Horizon Scan Report 0038, Mar. 2014.
National Institute for Health Research, "Point-of-Care Creatinine Testing for the Detection and Monitoring of Chronic Kidney Disease," NIHR Diagnostic Evidence Cooperative Oxford; Mar. 2014, p. 2 heading details of technology; p. 3, heading importance and table 1; p. 5, second paragraph.
NOVA Biomedical, "StatSensor Point-of-Care Whole Blood Creatinine and eGRF Testing," May 2008; [retrieved Mar. 8, 2018]. Retrieved from the Internet; <URL: http://novamed.dk/uf/30000_39999/38239/2027ea11fdbd525ddc1c17d1ab983a44.pdf>; p. 2, photograph; p. 8, heading docking station.
International Search Report and Written Opinion corresponding to International PCT Application PCT/US2018/015589 dated Mar. 22, 2018.

(Continued)

Primary Examiner — Ali Soroush
Assistant Examiner — Genevieve S Alley
(74) Attorney, Agent, or Firm — Sheppard Mullin Richter & Hampton LLP

(57) ABSTRACT

A method of affecting blood chemistry using a supplement may comprise: measuring a blood glucose level; determining a blood glucose level; and if the blood glucose level exceeds a threshold, administering a supplement comprising lysine, zinc, and vitamin C.

12 Claims, 7 Drawing Sheets

(56) References Cited

OTHER PUBLICATIONS

International Search Report and Written Opinion corresponding to International PCT Application PCT/US2018/015583 dated Mar. 26, 2018.
Medtronic "Guardian Real-Time Continuous Glucose Monitoring System" 2006; (retrieved Mar. 6, 2018).
Maurer, Dr. Richard, "HOMA-IR: What it is & why you should know yours," The Blood Code, Sep. 20, 2016, <https://www,thebloodcode.com/homa-ir-know/.
Nah et al., "Annals of Laboratory Medicine, Comparison of Urine Albumin-to-Creatinine Ratio (ACR) between ACR strip test and quantitative test in Prediabetes and Diabetes," Jan. 2017.
Clinitek Advantus Analyzer, Siemens, Operators Guide, Jun. 2006.
Sulochana et al., "Effect or oral supplementation of free amino acids in type 2 diabetic patients—a pilot clinical trial," Medical Science Monitor, 2002, 8(3), CR131-137.
Healthy Care Australia, Product Label for Super Lysine Cold Sore Relief, <http://healthycare.com.au/index.php/our-products/all-products/item/hc-super-lysine-cold-sore-relief-100-tablets>.
Zhu, English machine translation of CN 102772215.
Jayawardena et al., "Effects of zinc supplementation on diabetes mellitus: a systematic review and meta-analysis." Diabetology & Metabolic Syndrome, 2012, pp. 1-15, <http://www.nbci.nlm.nih.gov/pmc/articles/PMC3407731/>.

* cited by examiner

| CKD stage | GFR level (mL/min/1.73 m²) |
|---|---|
| Stage 1 | ≥ 90 |
| Stage 2 | 60 – 89 |
| Stage 3 | 30 – 59 |
| Stage 4 | 15 – 29 |
| Stage 5 | < 15 |

*FIG. 6*

INHIBITING CHRONIC BLOOD AND NEPHROLOGICAL DISORDERS USING LYSINE-BASED SUPPLEMENTS

RELATED APPLICATIONS

This application is a continuation of and claims the benefit of U.S. patent application Ser. No. 15/870,813 filed on Jan. 12, 2018, which is a continuation-in-part of U.S. patent application Ser. No. 15/817,574, filed on Nov. 20, 2017, which claims benefit of U.S. Provisional Patent Application No. 62/581,573, filed on Nov. 3, 2017, the contents all of which are incorporated herein by reference in their entirety.

FIELD OF THE INVENTION

The present disclosure is generally related to dietary supplements, and more specifically, embodiments of the present disclosure relate to the use of lysine, zinc, and vitamin C to inhibit chronic kidney disease (CKD).

BACKGROUND

Glycation is the bonding of a simple sugar to a protein or lipid molecule. Glycation may be either exogenous (i.e., outside the body) or endogenous (i.e., inside the body). Endogenous glycation mainly occurs in the bloodstream to absorbed simple sugars, such as glucose, fructose, and galactose. Glycation is the first change of these molecules in a slow multi-step process which leads to advanced glycation end products (AGEs). Because AGEs are irreversible end products of a glycation process, stopping the glycation process before AGEs form is important. AGEs may be benign, but many are implicated in many age-related chronic diseases such as diabetes, cardiovascular diseases, Alzheimer's disease, cancer, chronic kidney disease (CKD), atherosclerosis, peripheral neuropathy, and other sensory losses such as deafness. Preventing this process may also help regulate creatinine levels of people with diabetes and creatinine levels of people with CKD.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention.

FIG. 6 is a table illustrating the relationship between a stage of chronic kidney disease and the related glomerular filtration rate range, consistent with embodiments disclosed herein.

These figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present disclosure is directed towards treatment of CKD using supplements containing lysine, zinc, and vitamin C. More specifically, embodiments disclosed herein are directed towards methods for detecting the effectiveness of lysine, zinc, and vitamin C supplements in competing with existing protein and lipid molecules settled within the body to reduce the number of glycated proteins and to prevent AGEs. Lysine, zinc, and vitamin C supplements may also be used to treat chronic kidney disease (CKD). For example, combined supplement formulations of lysine, zinc, and vitamin C may interact with simple sugars that might otherwise interact with existing protein to create glycated proteins and AGEs that lead to various chronic health problems. For example, the supplement may comprise a range of about 500 mg to about 2000 mg of lysine, a range of about 50 mg to about 200 mg of zinc, and a range of about 50 mg to about 500 mg of vitamin C. In other embodiment, the ranges of lysine, zinc, or vitamin C may be different. The effectiveness of the lysine, zinc, and vitamin C supplements may be measured through bio-sample analysis, such as a blood test for hemoglobin A1c or for creatinine. The inclusion of zinc significantly increases the efficacy of a supplement containing only lysine. The inclusion of zinc allows for the reduction in dosage/pill size with same or better results. The inclusion of vitamin C may further reduce the effects of diabetes and CKD.

Figure 1:
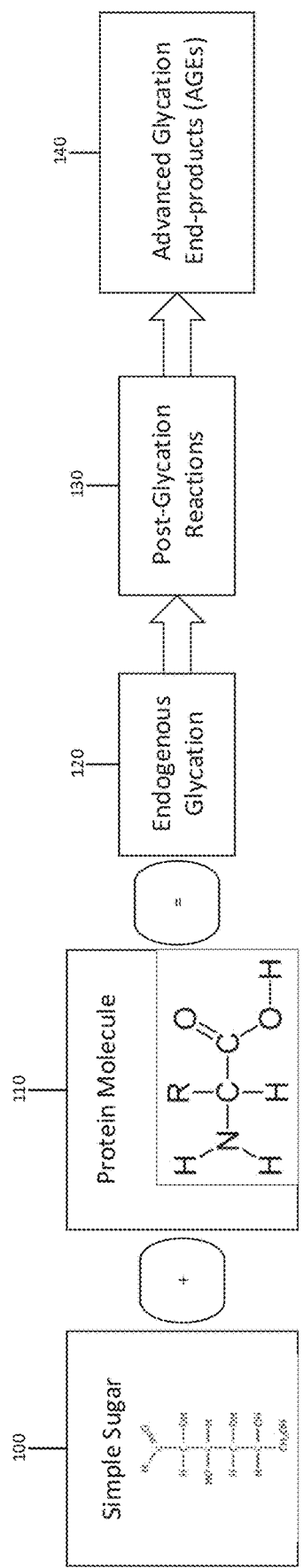
FIG. 1 is a diagram illustrating an example of endogenous glycation, consistent with embodiments disclosed herein.

FIG. 1 is a diagram illustrating an example of endogenous glycation. As illustrated in FIG. 1, the absorbed simple sugars 100 may include glucose. As is known in the art, the simple sugars may also include fructose and galactose. Fructose experiences up to ten times the amount of glycation activity compared to glucose. As an example, FIG. 1 illustrates the structural formula for glucose. Simple sugar 100 may interact with a protein molecule 110 resulting in endogenous glycation 120. As an example, the general structural formula for an amino acid is also illustrated in FIG. 1. Various other proteins may interact with the simple sugar 100. In another embodiment, various lipid molecules may interact with the simple sugar 100. In particular, with endogenous glycation, the covalent bonding between simple sugar 100 and protein molecule 110 may occur without the control of an enzyme. Endogenous glycation occurs mainly in the bloodstream.

Glycation 130 may be a first step before these new molecules undergo post glycation reactions 140, such as Schiff base and Amadori reactions. For example, the aldehyde group of a glucose molecule may combine with the amino group of a L-lysine molecule, from a protein molecule, to form a Schiff base. In essence, a double bond may be formed between the glucose's carbon atoms and the lysine's nitrogen atoms. The Amadori product rearranges the formation of the Schiff base. As a result, AGEs 150 may be formed. For example, when an Amadori product may be oxidized, AGEs 150 are formed. While some AGEs are benign, others may contribute to cardiovascular disease, chronic kidney disease, cancer, and other chronic diseases associated with diabetes.

Figure 2:
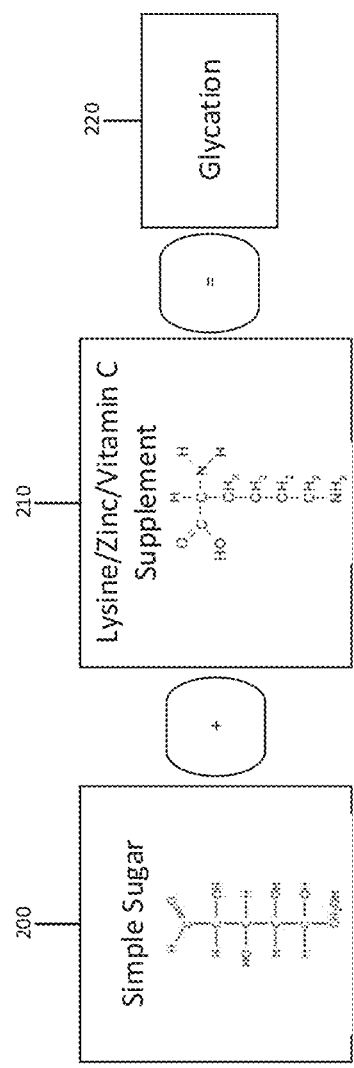
FIG. 2 is a diagram illustrating an example of glycation occurring with a supplement containing lysine, zinc, and vitamin C, consistent with embodiments disclosed herein.
Figure 3:
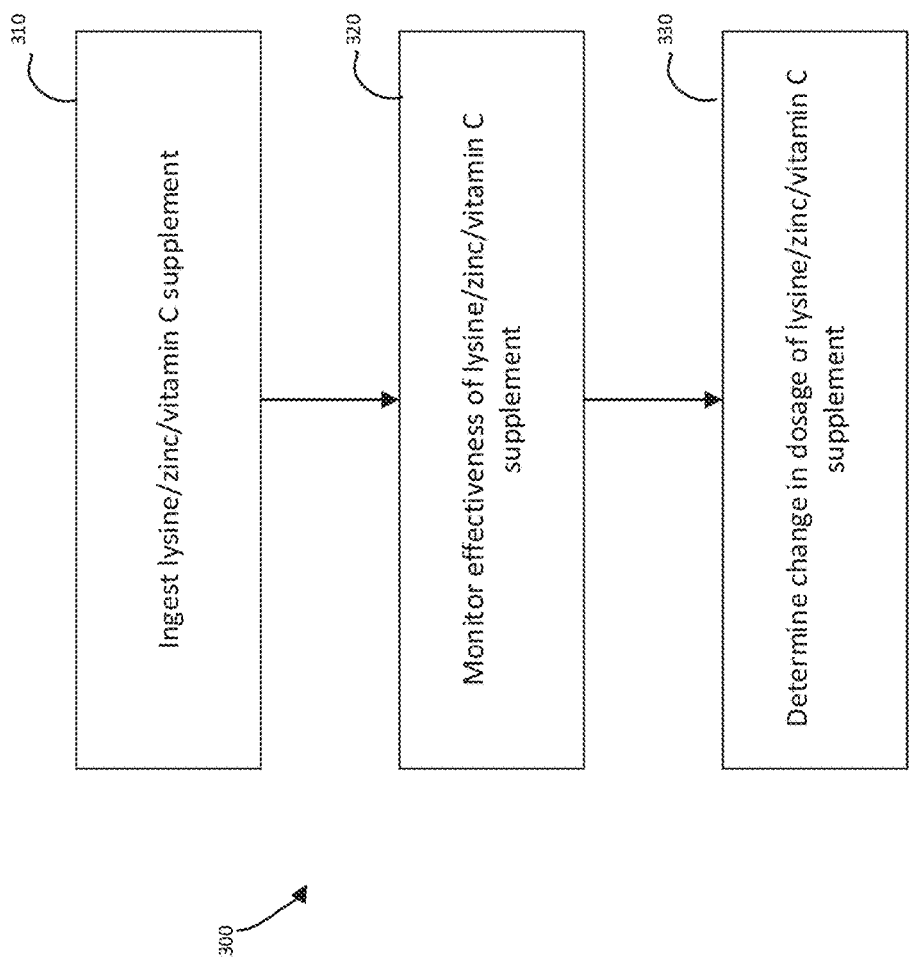
FIG. 3 is a flow chart illustrating an example method of monitoring the effectiveness of lysine, zinc, and vitamin C supplements from a bio-sample, consistent with embodiments disclosed herein.

FIG. 2 is a diagram illustrating an example of glycation occurring with a supplement containing lysine, zinc, and vitamin C. In this case, the simple sugars 200 interact with the lysine, zinc, and vitamin C supplement 210 instead of the protein molecule 110. As described above, Schiff bases form when the amino group of a lysine molecule, which is a part of a protein molecule, covalently bond with the aldehyde group of a glucose molecule. However, when a supplement containing lysine is administered, the aldehyde group of a glucose molecule may bind to the lysine instead of the lysine molecule portion of the protein molecule. The supplement may contain D-lysine or L-lysine. Glycation 220 may occur, but AGEs are prevented from occurring within the body, and glycated hemoglobin may be reduced. Even if Amadori products occur and AGEs form, they are not introduced into the body because the glycated lysine may be harmlessly removed through the urine. As set forth herein, it has been determined that the inclusion of zinc significantly increases the efficacy of a supplement containing lysine, thereby allowing for a significant reduction in dosage/pill size with same or better results. In some embodiments, a dietary supplement may include a combination of lysine, zinc, vitamin C and other nutritional supplements, e.g., vitamin B12, vitamin E, or other nutritional supplements. For example, a dietary supplement including lysine, zinc, and vitamin C may improve immune system functionality and lower glucose levels FIG. 3 is a flow chart illustrating an example method of monitoring the effectiveness of lysine, zinc, and vitamin C supplements from a bio-sample 300. For example, method 300 may include administering a lysine, zinc, and vitamin C supplement at step 310. For example, the supplement may comprise a range of about 500 mg to about 2000 mg of lysine, a range of about 50 mg to about 200 mg of zinc, and a range of about 50 mg to about 500 mg of vitamin C. In other embodiments, the ranges of lysine, zinc, or vitamin C may be different. In still other embodiments, the supplement may comprise lysine and zinc, lysine and vitamin C, lysine, zinc, and vitamin C, and/or other combinations. The lysine, zinc, and vitamin C supplement may be administered in a pill, gummy, tablet, shake, capsule, liquid extract, drink, or nutritional bar medium. The lysine, zinc, and vitamin C supplement may also come in various other mediums. The lysine portion of the lysine, zinc, and vitamin C supplement may be D-lysine or L-lysine. D-lysine, is not naturally produced within the body, and has similar chemical characteristics to L-lysine. Simple sugars may interact with D- and L-lysine in in lieu of free amino groups in structural proteins within the system. L-lysine occurs naturally in the body. Naturally occurring L-lysine may be a side-chain residue of ingested protein. L-lysine may have a bitter and/or sweet taste, making it more suitable for particular supplement mediums.

Method 300 may also include monitoring the effectiveness of the lysine, zinc, and vitamin C supplement at step 320. In some embodiments, effectiveness of the lysine treatment may be monitored by analyzing blood or urine samples. The glycated lysine may harmlessly pass through the urine upon interacting with simple sugars. A urine sample may be obtained and analyzed using a fructosamine test that measures glycated lysine. In other embodiments, a urine sample can be analyzed using a visual test. For example, some urine tests may expose the urine sample to a reagent which causes a color change indicating the concentration range of lysine within the urine. In some embodiments, a more precise test may be used to indicate quantitative levels of glycated lysine in the urine sample. In addition, the urine sample may also be used to monitor creatinine control, particularly useful for people with chronic kidney disease. As the lysine, zinc, and vitamin C supplement interacts with sugar, less hemoglobin may be glycated as a result. As a result, blood glucose levels and HbA1c levels may decrease. Moreover, the lysine, zinc, and vitamin C supplement may reduce creatinine levels.

In another embodiment, the lysine concentration may be monitored using an automatic reader. For example, an optical reader on a smartphone may be used to capture the lysine concentration measurements taken on a test. An optical reader may include a camera on a smartphone. The measurement may be captured by the optical reader using the test where the glycated lysine concentration was measured. In some embodiments, the value may be manually input into the automatic reader. An optical reader may capture the measurement and transmit the measurement to a data store. Depending on this value, the automatic reader may provide notifications on whether lysine supplements are appropriate to administer. The notification may include a pop-up, a vibration, or a noise. The notifications may continue over time. The period between notifications may increase over time. The notifications may be stopped by user input. As more data is stored, a more precise dosage of lysine supplements may be determined to be taken over a period of time.

Method 300 may also include determining any change in the dosage of the lysine, zinc, and vitamin C supplement, if necessary, as in step 330. In one embodiment, a visual cue test may help determine whether more or less lysine, zinc, and vitamin C supplements may need to be taken. In another embodiment, a specific value on a test may indicate whether more or less lysine supplements should be taken.

Figure 4:
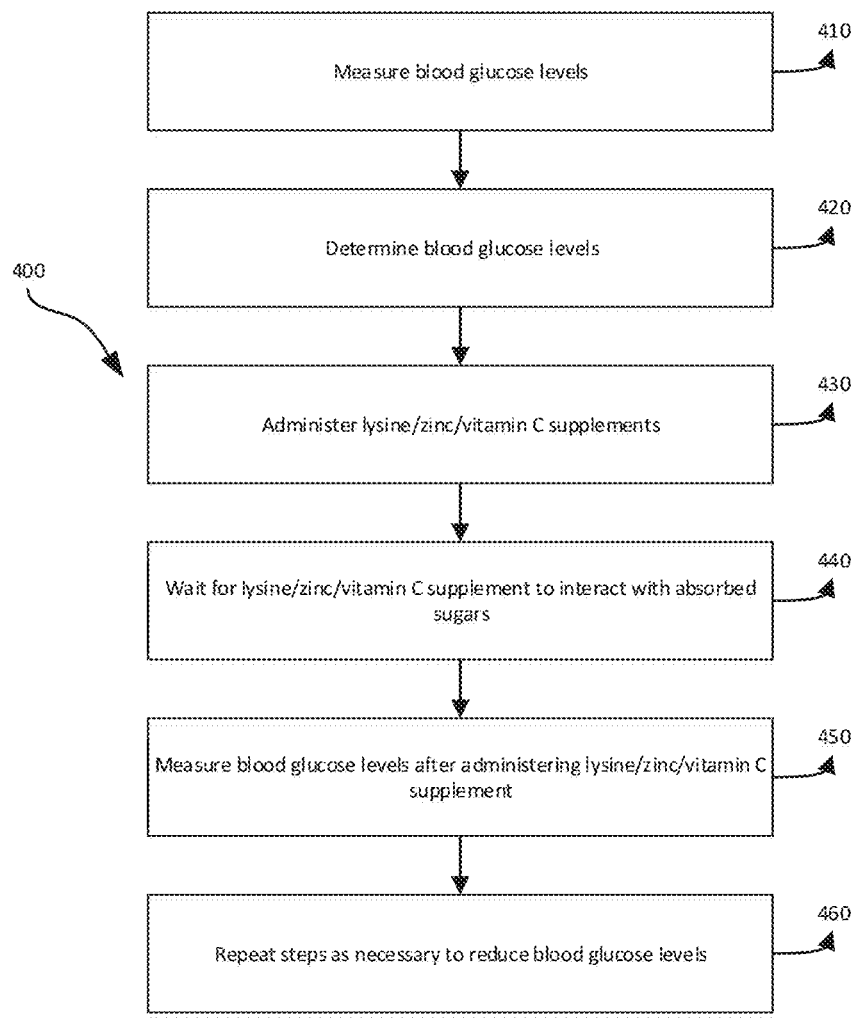
FIG. 4 is a flow chart illustrating an example method of treating diabetes using lysine, zinc, and vitamin C supplements, consistent with embodiments disclosed herein.

FIG. 4 is a flow chart illustrating an example method of treating diabetes using lysine, zinc, and vitamin C supplements 400. For example, method 400 may include measuring the current blood glucose level from a test at step 410. For example, the supplement may comprise a range of about 500 mg to about 2000 mg of lysine, a range of about 50 mg to about 200 mg of zinc, and a range of about 50 mg to about 500 mg of vitamin C. In other embodiments, the ranges of lysine, zinc, or vitamin C may be different. In still other embodiments, the supplement may comprise lysine and zinc, lysine and vitamin C, lysine, zinc, and vitamin C, and/or other combinations. The test may include a fingerprick test that quantitatively indicates a blood glucose level. Method 400 may also include determining blood glucose level at step 420. Using the blood glucose level measurement from step 410, it may be determined that the blood glucose level is too high. Method 400 may also include administering lysine, zinc, and vitamin C supplements, based on blood glucose level at step 430. If the blood glucose level is too high, it may be appropriate to administer lysine, zinc, and vitamin C supplements. The supplement may be administered in a pill, gummy form, tablet, powder for a shake, capsule, liquid extract, drink, or nutritional bar medium. The lysine, zinc, and vitamin C supplement may also come in various other mediums. The appropriate dosage will depend on the measured blood glucose level.

Method 400 may also include waiting for lysine to interact with absorbed sugars at step 440. After administering the lysine, zinc, and vitamin C supplement, a period of time should pass to allow the supplement to interact with the sugar. Method 400 may also include measuring blood glucose level after administering lysine, zinc, and vitamin C supplement at step 450. After the appropriate period of time, the blood glucose level may be tested again to monitor any changes before and after the supplement was taken. If blood glucose levels are within an appropriate range, no more supplements may need to be taken. Method 400 may also include repeating the above steps as necessary to reduce blood glucose levels at step 460. If the measured blood glucose level taken after the lysine, zinc, and vitamin C supplement is not within an appropriate range, additional supplements may need to be taken to reduce blood glucose levels.

Figure 5:
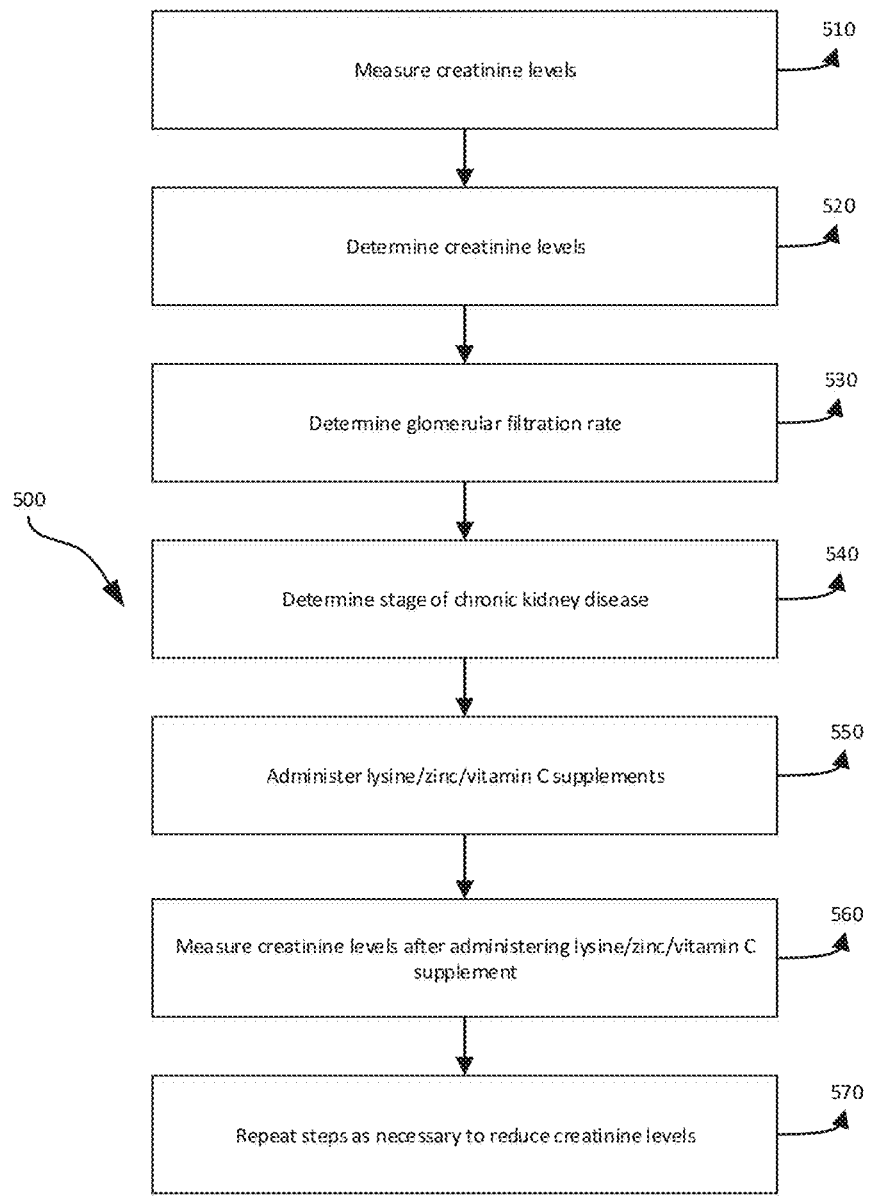
FIG. 5 is a flow chart illustrating an example method of treating chronic kidney disease using lysine, zinc, and vitamin C supplements, consistent with embodiments disclosed herein.

FIG. 5 is a flow chart illustrating an example method of treating CKD using supplements with lysine, zinc, and/or vitamin C 500. For example, method 500 may include measuring the current creatinine levels from a test at step 510. For example, the supplement may comprise a range of about 500 mg to about 2000 mg of lysine, a range of about 50 mg to about 200 mg of zinc, and a range of about 50 mg to about 500 mg of vitamin C. In other embodiments, the ranges of lysine, zinc, or vitamin C may be different. In still other embodiments, the supplement may comprise lysine and zinc, lysine and vitamin C, lysine, zinc, and vitamin C, and/or other combinations. The test may include a fingerprick test that quantitatively indicates a creatinine level. Method 500 may also include determining creatinine levels at step 520. Method 500 may also include determining a glomerular filtration rate (GFR) at step 530. Using the creatinine concentration measurement from step 510, the GFR may be determined. Method 500 may also include determining a stage of CKD at step 540. Using the GFR, an individual's weight, age, height, and other factors, the CKD may be determined. A GFR greater than about 90 milliliters per minute per 1.73 square meters might indicate stage 1 CKD. A GFR between about 60 and about 90 milliliters per minute per 1.73 square meters might indicate stage 2 CKD. A GFR between about 30 and about 60 milliliters per minute per 1.73 square meters might indicate stage 3 CKD. A GFR between about 15 and about 30 milliliters per minute per 1.73 square meters might indicate stage 4 CKD. A GFR less than about 15 milliliters per minute per 1.73 square meters might indicate stage 5 CKD. FIG. 6 more clearly illustrates this relationship between GFR and the stage of CKD.

Method 500 may also include administering supplements with lysine, zinc, and/or vitamin C, based on GFR at step 550. If the creatinine level is too high, it may be appropriate to administer supplements with lysine, zinc, and/or vitamin C. The supplement may be administered in a pill, gummy form, tablet, powder for a shake, capsule, liquid extract, drink, or nutritional bar medium. The supplements with lysine, zinc, and/or vitamin C may also come in various other mediums. The appropriate dosage will depend on the measured creatinine level.

Method 500 may also include measuring a creatinine level after administering supplements with lysine, zinc, and/or vitamin C at step 560. After the appropriate period of time, the creatinine level may be tested again to monitor any changes before and after the supplement was taken. If creatinine levels are within an appropriate range, no more supplements may need to be taken. Method 500 may also include repeating the above steps as necessary to reduce creatinine levels at step 570. If the measured creatinine level taken after the supplements with lysine, zinc, and/or vitamin C is not within an appropriate range, additional supplements may need to be taken to reduce blood glucose levels.

Figure 7:
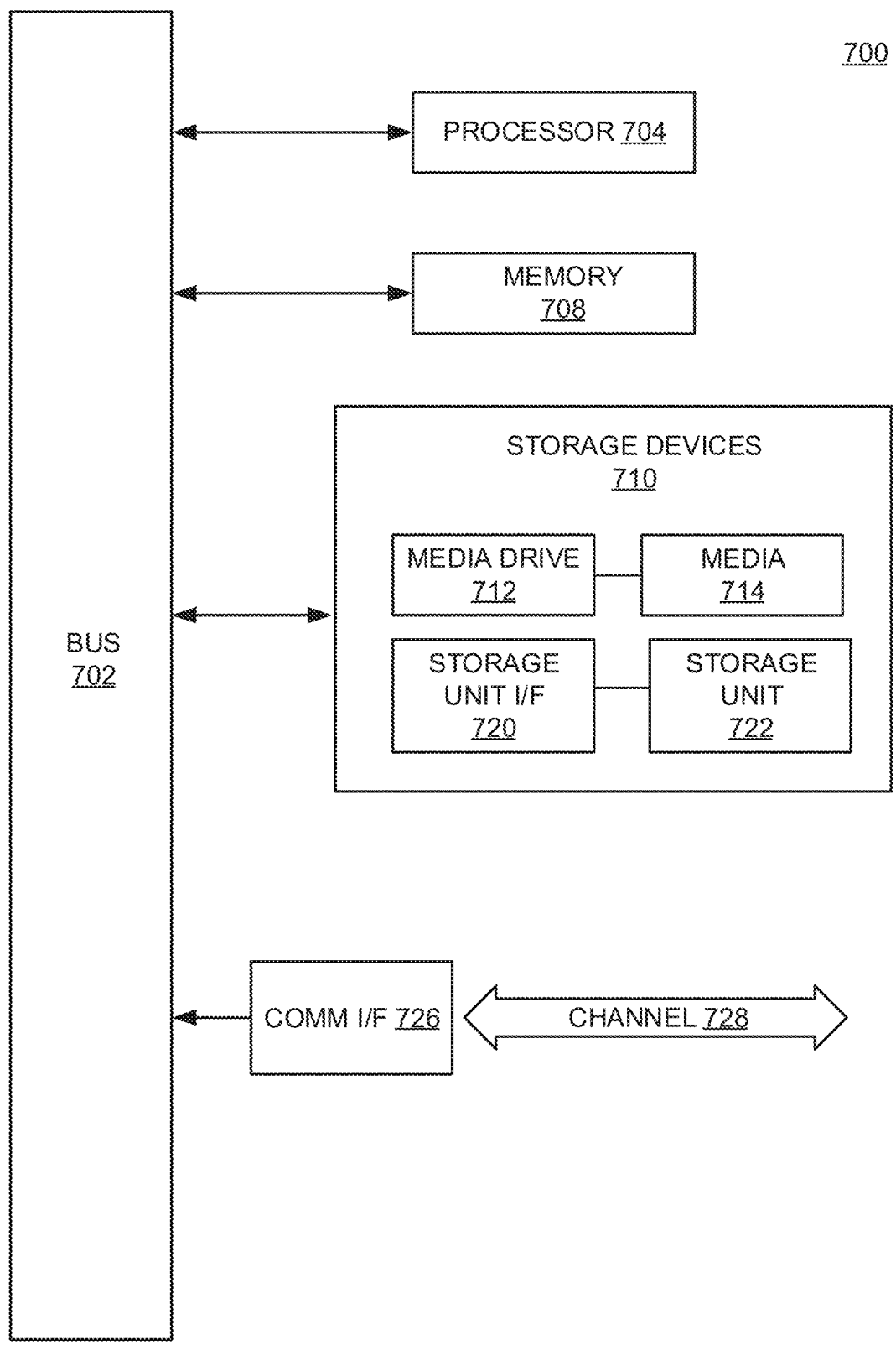
FIG. 7 is a diagram illustrating an exemplary computing module that may be used to implement any of the embodiments disclosed herein.

As used herein, the terms logical circuit and engine might describe a given unit of functionality that may be performed in accordance with one or more embodiments of the technology disclosed herein. As used herein, either a logical circuit or an engine might be implemented utilizing any form of hardware, software, or a combination thereof. For example, one or more processors, controllers, ASICs, PLAs, PALs, CPLDs, FPGAs, logical components, software routines or other mechanisms might be implemented to make up a engine. In implementation, the various engines described herein might be implemented as discrete engines or the functions and features described may be shared in part or in total among one or more engines. In other words, as would be apparent to one of ordinary skill in the art after reading this description, the various features and functionality described herein may be implemented in any given application and may be implemented in one or more separate or shared engines in various combinations and permutations. Even though various features or elements of functionality may be individually described or claimed as separate engines, one of ordinary skill in the art will understand that these features and functionality may be shared among one or more common software and hardware elements, and such description shall not require or imply that separate hardware or software components are used to implement such features or functionality.

Where components, logical circuits, or engines of the technology are implemented in whole or in part using software, in one embodiment, these software elements may be implemented to operate with a computing or logical circuit capable of carrying out the functionality described with respect thereto. One such example logical circuit is shown in FIG. 7. Various embodiments are described in terms of this example logical circuit 700. After reading this description, it will become apparent to a person skilled in the relevant art how to implement the technology using other logical circuits or architectures.

Referring now to FIG. 7, computing system 700 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Logical circuit 700 might also represent computing capabilities embedded within or otherwise available to a given device. For example, a logical circuit might be found in other electronic devices such as, for example, digital cameras, navigation systems, cellular telephones, portable computing devices, modems, routers, WAPs, terminals and other electronic devices that might include some form of processing capability.

Computing system 700 might include, for example, one or more processors, controllers, control engines, or other processing devices, such as a processor 704. Processor 704 might be implemented using a general-purpose or special-purpose processing engine such as, for example, a microprocessor, controller, or other control logic. In the illustrated example, processor 704 is connected to a bus 702, although any communication medium may be used to facilitate interaction with other components of logical circuit 700 or to communicate externally.

Computing system 700 might also include one or more memory engines, simply referred to herein as main memory

708. For example, preferably random access memory (RAM) or other dynamic memory, might be used for storing information and instructions to be executed by processor 704. Main memory 708 might also be used for storing temporary variables or other intermediate information during execution of instructions to be executed by processor 704. Logical circuit 700 might likewise include a read only memory ("ROM") or other static storage device coupled to bus 702 for storing static information and instructions for processor 704.

The computing system 700 might also include one or more various forms of information storage mechanism 710, which might include, for example, a media drive 712 and a storage unit interface 720. The media drive 712 might include a drive or other mechanism to support fixed or removable storage media 714. For example, a hard disk drive, a floppy disk drive, a magnetic tape drive, an optical disk drive, a CD or DVD drive (R or RW), or other removable or fixed media drive might be provided. Accordingly, storage media 714 might include, for example, a hard disk, a floppy disk, magnetic tape, cartridge, optical disk, a CD or DVD, or other fixed or removable medium that is read by, written to or accessed by media drive 712. As these examples illustrate, the storage media 714 can include a computer usable storage medium having stored therein computer software or data.

In alternative embodiments, information storage mechanism 710 might include other similar instrumentalities for allowing computer programs or other instructions or data to be loaded into logical circuit 700. Such instrumentalities might include, for example, a fixed or removable storage unit 722 and an interface 720. Examples of such storage units 722 and interfaces 720 can include a program cartridge and cartridge interface, a removable memory (for example, a flash memory or other removable memory engine) and memory slot, a PCMCIA slot and card, and other fixed or removable storage units 722 and interfaces 720 that allow software and data to be transferred from the storage unit 722 to logical circuit 700.

Logical circuit 700 might also include a communications interface 726. Communications interface 726 might be used to allow software and data to be transferred between logical circuit 700 and external devices. Examples of communications interface 726 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 726 might typically be carried on signals, which can be electronic, electromagnetic (which includes optical) or other signals capable of being exchanged by a given communications interface 726. These signals might be provided to communications interface 726 via a channel 728. This channel 728 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 708, storage unit 720, media 714, and channel 728. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the logical circuit 700 to perform features or functions of the disclosed technology as discussed herein.

Although FIG. 7 depicts a computer network, it is understood that the disclosure is not limited to operation with a computer network, but rather, the disclosure may be practiced in any suitable electronic device. Accordingly, the computer network depicted in FIG. 7 is for illustrative purposes only and thus is not meant to limit the disclosure in any respect.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent engine names other than those depicted herein can be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "engine" does not imply that the components or functionality described or claimed as part of the engine are all configured in a common package. Indeed, any or all of the various components of an engine, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of monitoring blood glucose levels, the method comprising:
   measuring a current blood glucose level of an individual from a biochemistry test;
   determining the current blood glucose level; and
   administering a supplement to the individual consisting of lysine, zinc, and vitamin C.

2. The method of claim 1, wherein the test comprises a fingerprick test that quantitatively indicates the current blood glucose level.

3. The method of claim 1, further comprising displaying, on a graphical user interface, the current blood glucose level.

4. The method of claim 1, wherein the test comprises a fingerprick test that uses visual cues to indicate the current blood glucose level.

5. The method of claim 1, further comprising:
   measuring a second blood glucose level after administering the supplement; and
   administering a second dose of the supplement comprising lysine, zinc, and vitamin C to reduce the second blood glucose level.

6. The method of claim 1, wherein the supplement consists of a range of about 500 mg to about 3000 mg of lysine.

7. The method of claim 1, wherein the supplement consists of less than about 200 mg of zinc.

8. The method of claim 1, wherein the supplement consists of a range of about 50 mg to about 500 mg of vitamin C.

9. The method of claim 1, wherein the supplement consists of a range of about 500 mg to about 3000 mg of lysine, a range of less than about 200 mg of zinc, and a range of about 50 mg to about 500 mg vitamin C.

10. The method of claim 1, wherein a lysine portion of the supplement comprises D-lysine.

11. The method of claim 1, wherein a lysine portion of the supplement comprises L-lysine.

12. The method of claim 1, further comprising:
    measuring a current HbA1c level of an individual from the biochemistry test;
    determining the current HbA1c level; and
    administering the supplement to the individual comprising lysine, zinc, and vitamin C to reduce the current HbA1c level.

* * * * *